(12) United States Patent
Selaru et al.

(10) Patent No.: US 10,441,760 B2
(45) Date of Patent: Oct. 15, 2019

(54) SELF-ACTUATING CHEMOMECHANICAL DEVICES FOR DELIVERY AND EXTENDED RELEASE OF THERAPEUTIC AGENTS IN THE GASTROINTESTINAL TRACT

(71) Applicant: THE JOHNS HOPKINS UNIVERSITY, Baltimore, MD (US)

(72) Inventors: Florin M. Selaru, Catonsville, MD (US); David H. Gracias, Baltimore, MD (US); Joyce Breger, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/195,446

(22) Filed: Mar. 3, 2014

(65) Prior Publication Data

US 2014/0249499 A1    Sep. 4, 2014

Related U.S. Application Data

(60) Provisional application No. 61/771,448, filed on Mar. 1, 2013.

(51) Int. Cl.
*A61M 31/00*    (2006.01)

(52) U.S. Cl.
CPC .................. *A61M 31/002* (2013.01)

(58) Field of Classification Search
CPC ............... A61K 9/00; A61M 31/002
See application file for complete search history.

(56) References Cited

U.S. PATENT DOCUMENTS

2004/0158274 A1* 8/2004 WasDyke .......... A61F 2/01
606/200
2011/0125091 A1* 5/2011 Abbate .......... A61F 2/186
604/96.01
2014/0207019 A1 7/2014 Kalloo et al.

FOREIGN PATENT DOCUMENTS

WO    2009/111737 A1    9/2009
WO    WO2009111737    *    9/2009    .............. B81C 1/00
WO    2012/154511 A2    11/2012

OTHER PUBLICATIONS

Morishita, M. et al., "Is the oral route possible for peptide and protein drug delivery?", Drug Discov. Today, 2006, pp. 905-910, vol. 11.
Bassik, N. et al., "Enzymatically triggered actuation of miniaturized tools", J. Am. Chem. Soc., 2010, pp. 16314-16317, vol. 132 No. 46.
(Continued)

*Primary Examiner* — Imani N Hayman
(74) *Attorney, Agent, or Firm* — Casimir Jones, S.C.; Jeffrey W. Childers

(57) ABSTRACT

The presently disclosed delivery systems utilize microtools, also referred to as theragrippers, to deliver a drug or other therapeutic agent to targeted tissue. More particularly, the drug delivery system and methods provide a delivery system that is capable of anchoring to a tissue site and then delivering a drug or therapeutic agent to the tissue directly to or in the vicinity of the site over an extended period of time. Any number of theragrippers may be deployed as desired to deliver different doses of a desired drug or therapeutic agent. The theragrippers also can be biodegradable such that they remain in place for an extended period of time and then degrade without adversely affecting the surrounding tissue.

15 Claims, 13 Drawing Sheets

(56) References Cited

OTHER PUBLICATIONS

Colombo, P. et al., "Novel platforms for oral drug delivery", Pharm. Res., 2009, pp. 601-611, vol. 26 No. 3.
Siegel, R. et al., "Overview of controlled release mechanisms. In: Fundamentals and Applications of Controlled Release Drug Delivery", 2012, Controlled Release Society.
Basit, AW., "Advanced in colonic drug delivery", 2005, Drugs, vol. 65.
Lissner, D. et al., "Ulcerative colitis: current and future treatment strategies", Digestive Diseases, 2013, pp. 91-94, vol. 31.
Cheifetz, AS. "Management of active Crohn disease", Journal of the American Medical Association, 2013, pp. 2150-2158, vol. 309.
Lee, PI et al., "Probing the mechanisms of drug release from hydrogels", Journal of Controlled Release, 1991, pp. 229-236, vol. 16.
Tao, SL et al., "Microfabricated drug delivery systems: from particles to pores", Advanced Drug Delivery Reviews, 2003, pp. 315-328, vol. 55.
Lamprecht, A. et al., "A pH-senstive microsphere system for the colon delivery of tacrolimus containing nanoparticles", Journal of Controlled Release, 2005, pp. 337-346, vol. 104.
Guan, JJ et al., "Fabrication of polymeric microparticles for drug delivery by soft lithography", Biomaterials, 2006, pp. 4034-4041, vol. 27.
De Leede, LGL et al., "Rate-controlled rectal drug delivery in man with a hydrogel preparation", Journal of Controlled Release, 1986, pp. 17-24, vol. 4.
Guan, JJ et al., "Fabrication of particulate reservoir-containing, capsulelike, and self-folding polymer microstructures for drug delivery", Small, 2007, pp. 412-418, vol. 3.
Brazel, CS et al., "Pulsatile local delivery of thrombolytic and antithrombotic agents using poly(N-sopropylacrylamide-co-methacrylic acid) hydrogels", Journal of Controlled Release, 1996, pp. 57-64, vol. 39.
Tao, SL et al., "Gastrointestinal patch systems for oral drug delivery", Drug Discovery Today, 2005, pp. 909-915, vol. 10.
He, HY et al., "An oral delivery device based on self-folding hydrogels", Journal of Controlled Release, 2006, pp. 339-346, vol. 110.
Dadsetan, M. et al., "A stimuli-responsive hydrogel for doxorubicin delivery", Biomaterials, 2010, pp. 8051-8062, vol. 31.
Chirra, HD et al., "Multi-reservoir bioadhesive microdevices for independent rate-controlled delivery of multiple drugs", Small, 2012, pp. 3839-3846, vol. 8.
Bernards, DA et al., "Nanostructured thin film polymer devices for constant-rate protein delivery", Nanoletters, 2012, pp. 5355-5361, vol. 12.
Gupta, P. et al., "Hydrogels: from controlled release to pH-responsive drug delivery", Drug Discovery Today, 2002, pp. 569-579, vol. 7.
Chirra, HD et al., "Emerging microtechnologies for the development of oral drug delivery devices", Advanced Drug Delivery, 2012, pp. 1569-1578, vol. 64.
Guan, J. et al., "Self-folding of three-dimensional hydrogel microstructures", The Journal of Physical Chemistry B, 2005, pp. 23134-23137, vol. 109.
Bassik, N. et al., "Photolithogreaphically patterned smart hydrogel based bilayer actuators", Polymer, 2010, pp. 6093-6098, vol. 51.
Ionov, L., "Soft microorigami: self-folding polymer films", Soft Matter, 2011, pp. 6786-6791, vol. 7.
Shim, TS et al., "Controlled origami folding of hydrogel bilayers with sustained reversibility for robust microcarriers", Angewandte Chemie, 2011, pp. 1420-1423, vol. 51.
Stoychev, G. et al., "Shape-programmed folding of stimuli-responsive polymer bilayers", ACS Nano, 2012, pp. 3925-3934, vol. 6.
Gracias, DH, "Stimuli responsive self-folding using thin polymer films", Current Opinion in Chemical Engineering, 2013, pp. 112-119, vol. 2.
Wu, ZL et al., "Three-dimensional shape transformations of hydrogel sheets induced by small-scale modulation of internal stresses", Nature Communications, 2013, pp. 1586, vol. 4.
Leong, TG et al., "Tetherless thermobiochemically actuated microgrippers", Proceedings of the National Academy Sciences, 2009, pp. 703-708, vol. 106.
Gultepe, ER et al., "Biopsy with thermally-responsive untethered microtools", Advanced Materials, 2013, pp. 514-519, vol. 25.
Gultepe, E. et al., "Biologic tissue sampling with untethered microgrippers", Gastroenterology, 2013, pp. 691-693, vol. 144.
Oh, KS et al., Hydrogels-based drug delivery system with molecular imaging. In: Biomedical Applications of Hydrogels Handbook, 2010, Springer.
Vilar, G. et al., "Polymers and drug delivery systems", Current Drug Delivery, 2012, pp. 367-394, vol. 9.
Langer, RS et al., "Present and future applications of biomaterials in controlled drug delivery systems", Biomaterials, 1981, pp. 201-214, vol. 2.
Gurny, R. et al., "Modelling of sustained release of water-soluble drugs from porous, hydrophobic polymers", Biomaterials, 1982, pp. 27-32, vol. 3.
Shaikh, R. et al., "Mucoadhesive drug delivery systems", J. Pharm. Bioallied. Sci., 2011, pp. 89-100, vol. 3.
Kremser, C. et al., "In vivo determination of the time and location of mucoadhesive drug delivery systems disintegration in the gastrointestinal tract", Magnetic Resonance Imaging, 2008, pp. 638-643, vol. 26.
Fernandes et al., "Self-folding polymeric containers for encapsulation and delivery of drugs", Adv Drug Deliv Rev. Nov. 2012;64(14):1579-89, Mar. 6, 2012.
Randall et al., "3D lithographically fabricated nanoliter containers for drug delivery", Advanced Drug Delivery Reviews 59, 1547-1561, 2007.

* cited by examiner

SELF-ACTUATING CHEMOMECHANICAL DEVICES FOR DELIVERY AND EXTENDED RELEASE OF THERAPEUTIC AGENTS IN THE GASTROINTESTINAL TRACT

CROSS-REFERENCE TO RELATED APPLICATIONS

This application claims the benefit of U.S. Provisional Application No. 61/771,448, filed Mar. 1, 2013, which is incorporated herein by reference in its entirety.

FEDERALLY SPONSORED RESEARCH OR DEVELOPMENT

This invention was made in part with United States Government support under OD004346 awarded by the National Institutes of Health (HIB). The U.S. Government has certain right in the invention.

BACKGROUND

Efficient delivery of therapeutic agents, such as a drug, to a subject in need of therapeutic treatment can be profoundly affected by the characteristics of the delivery vehicle. Aside from activity in vivo, the ideal therapeutic agent can be delivered to a site associated with a disease, condition, disorder, or symptom thereof, where it has a duration of action that preferably is long compared to the duration of the disease, condition, disorder, or symptom. One of the most challenging tasks facing the therapeutic treatment of mucosal gastrointestinal (GI) disorders, and other non-GI diseases, conditions, disorders, or symptoms that can be treated through access to the GI tract, is how to effectively and safely administer therapeutic agents via an oral or rectal route that is relatively non-invasive and acceptable to patients. Morishita and Peppas (2006).

Recent progress in the chemical composition and characteristics of delivery vehicles for oral or rectal administration allows for the sustained release of therapeutic agents from polymer matrices and their controlled delivery to a subject over the course of several days (up to a month). In the current state of the art of oral medications, however, therapeutic agents, such as drugs, are encapsulated in pills or capsules and move along the GI tract in a matter of hours after entering the body. The ideal therapeutic agent would be taken once and would provide adequate local or systemic levels of the active agent for the duration of the disease, condition, disorder, or symptom thereof. One current limitation of such a drug delivery paradigm is the lack of a system that can be anchored to the diseased site for a time sufficient to provide efficacious therapy and to resist expulsion by motility or other physiologic motor activity.

SUMMARY

In one aspect, the presently disclosed subject matter provides a system for delivering one or more therapeutic agents to a tissue site in a subject, the system comprising: (a) a multi-fingered mechanical gripping module comprising a plurality of sharp or tapered tips, wherein the fingers comprise a metal, a stiff polymer, or combinations thereof, the mechanical gripping module having a first configuration capable of being actuated to at least a second configuration in response to one or more stimuli, wherein the mechanical gripping module is adapted to grasp tissue at the tissue site when in the at least second configuration; and (b) a chemical module comprising a thin film, porous material, capsule, or reservoir patterned on the mechanical gripping module, wherein the thin film, porous material, capsule, or reservoir comprises the one or more therapeutic agents.

In other aspects, the presently disclosed subject matter provides a method for delivering one or more therapeutic agents to a tissue site in a subject, the method comprising: (a) introducing to the subject a plurality of delivery systems comprising: (i) a multi-fingered mechanical gripping module comprising a plurality of sharp or tapered tips, wherein the fingers comprise a metal, a stiff polymer, or combinations thereof, the mechanical gripping module having a first configuration capable of being actuated to at least a second configuration in response to one or more stimuli, wherein the mechanical gripping module is adapted to grasp tissue at the tissue site when in the at least second configuration; and (ii) a chemical module comprising a thin film, porous material, capsule, or reservoir patterned on the mechanical gripping module, wherein the thin film, porous material, capsule, or reservoir comprises the one or more therapeutic agents; (b) contacting the plurality of delivery systems to the tissue site; (c) altering a configuration of the plurality of theragrippers from a first configuration to a second configuration while in contact with the tissue, the second configuration adapted such that the mechanical module grasps the tissue at a discrete location; and (d) releasing one or more therapeutic agents from the plurality of delivery systems.

In some aspects, the delivering of one or more therapeutic agents to a tissue site in a subject comprises treating a subject for a disease, condition, disorder, or symptom.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
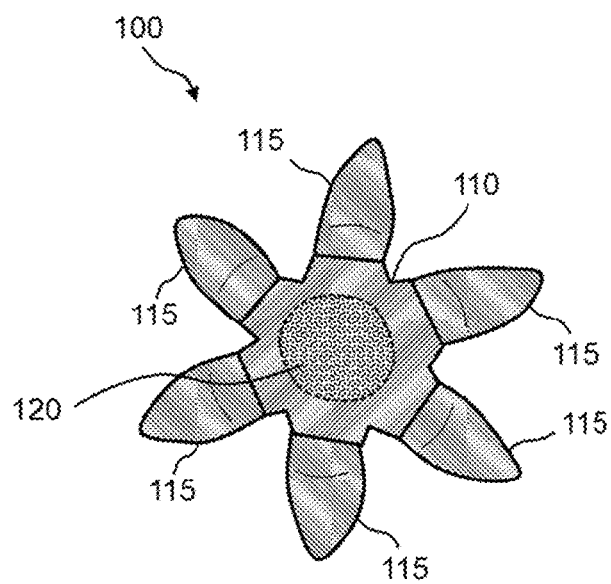
Figure 1B:
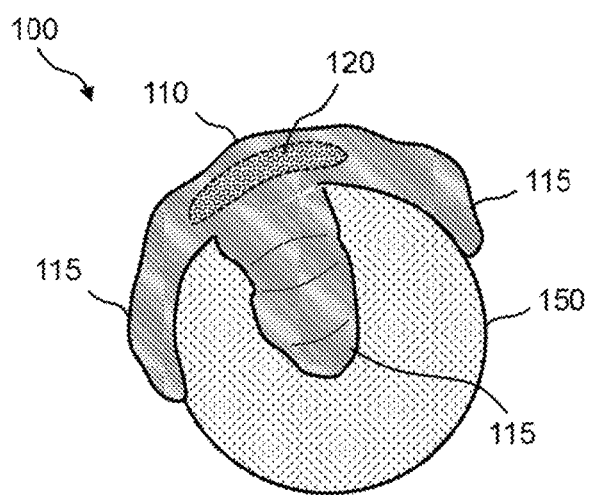
Figure 2A:
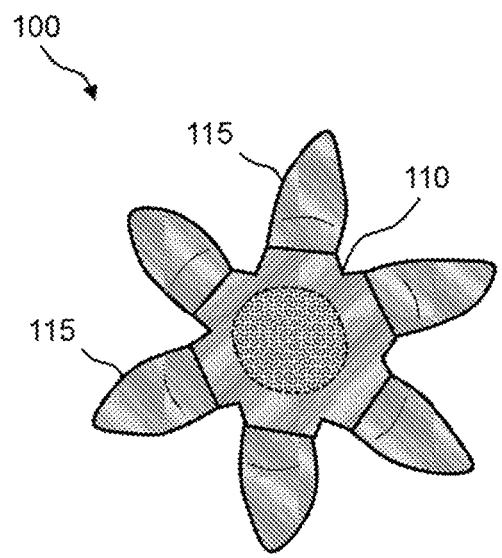
Figure 2B:
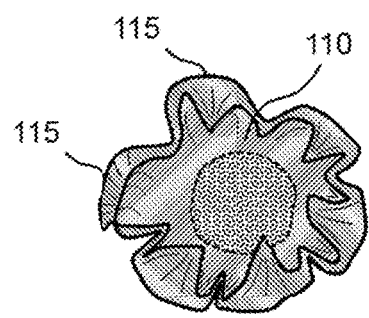
Figure 2C:
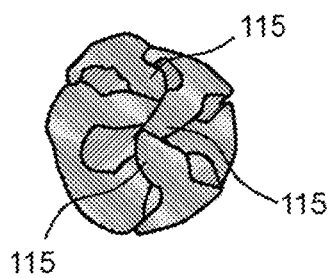
Figure 3:
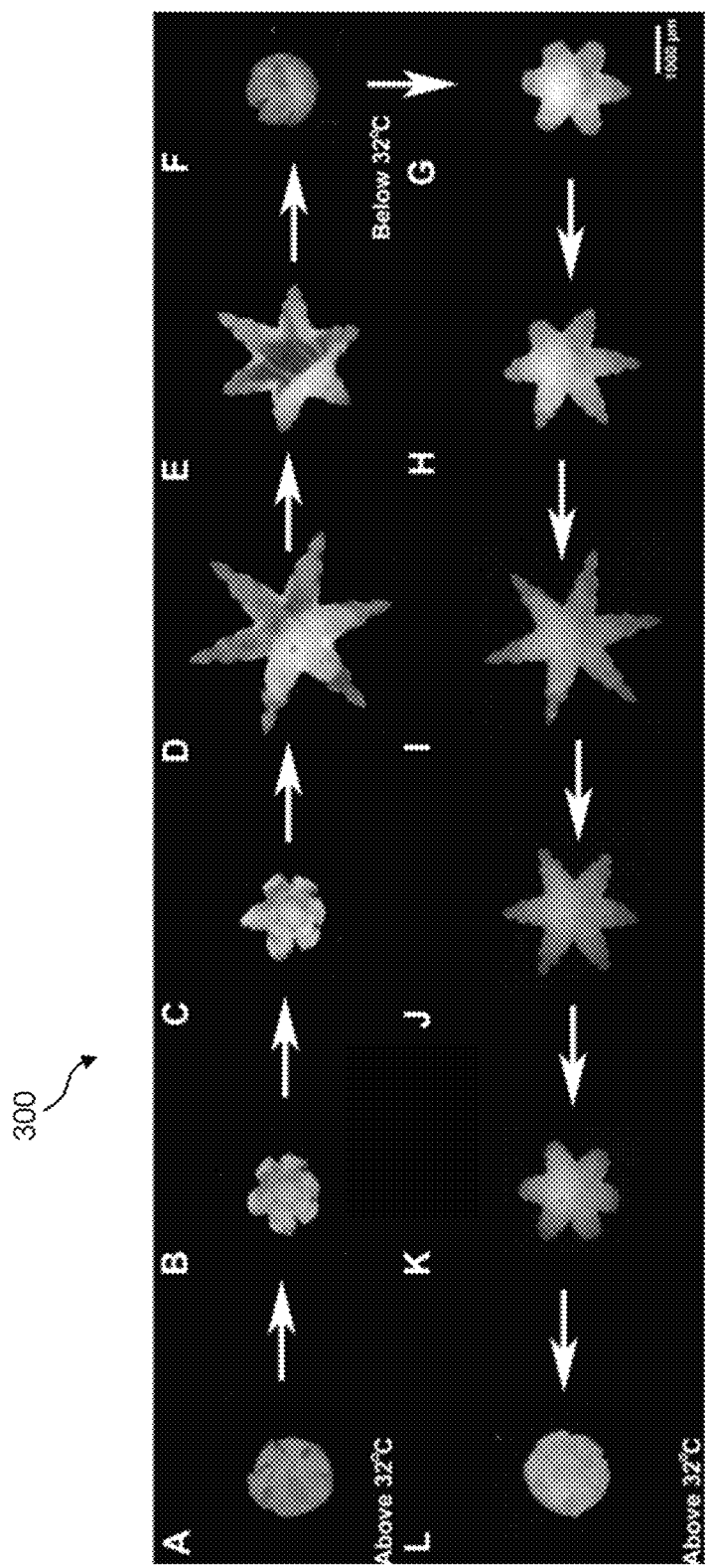
Figure 4A:
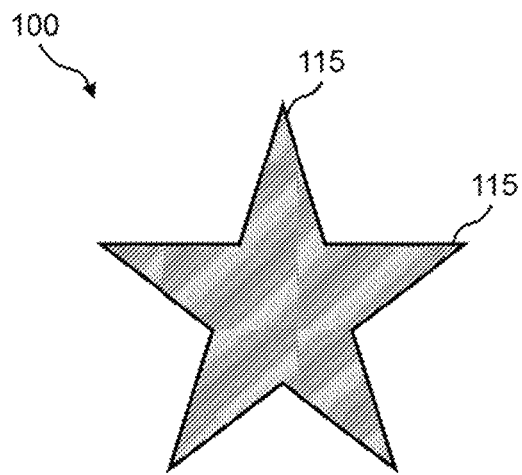
Figure 4B:
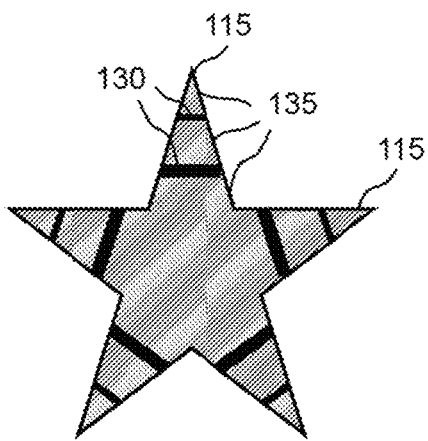
Figure 4C:
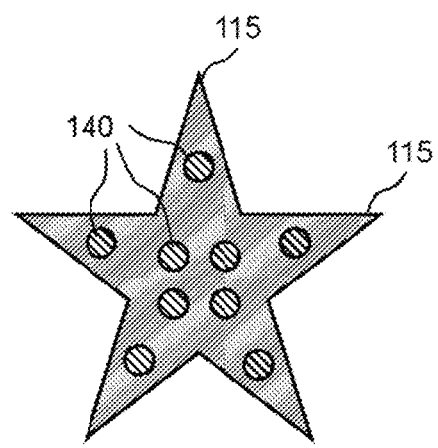
Figure 5A:
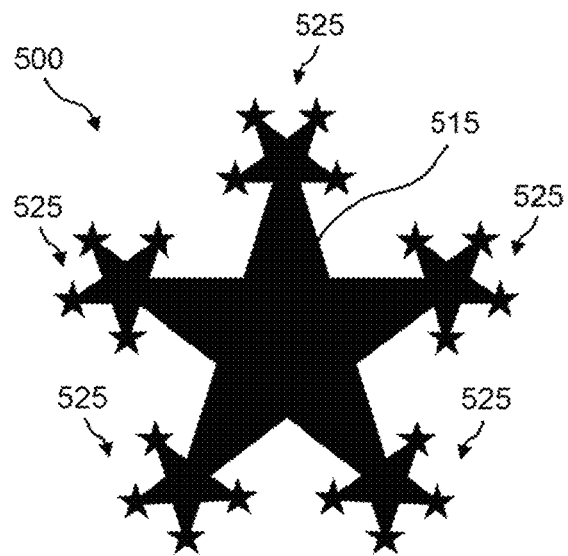
Figure 5B:
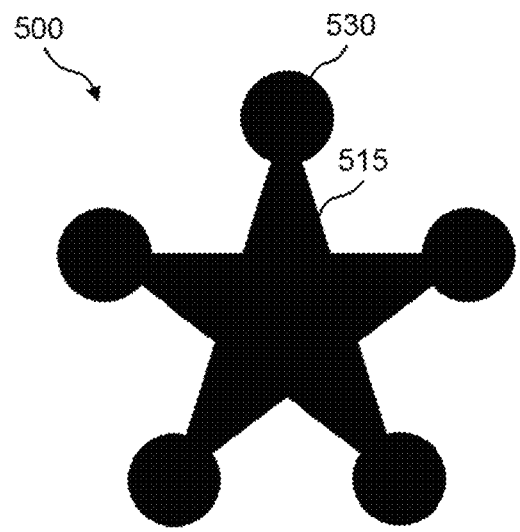
Figure 6:
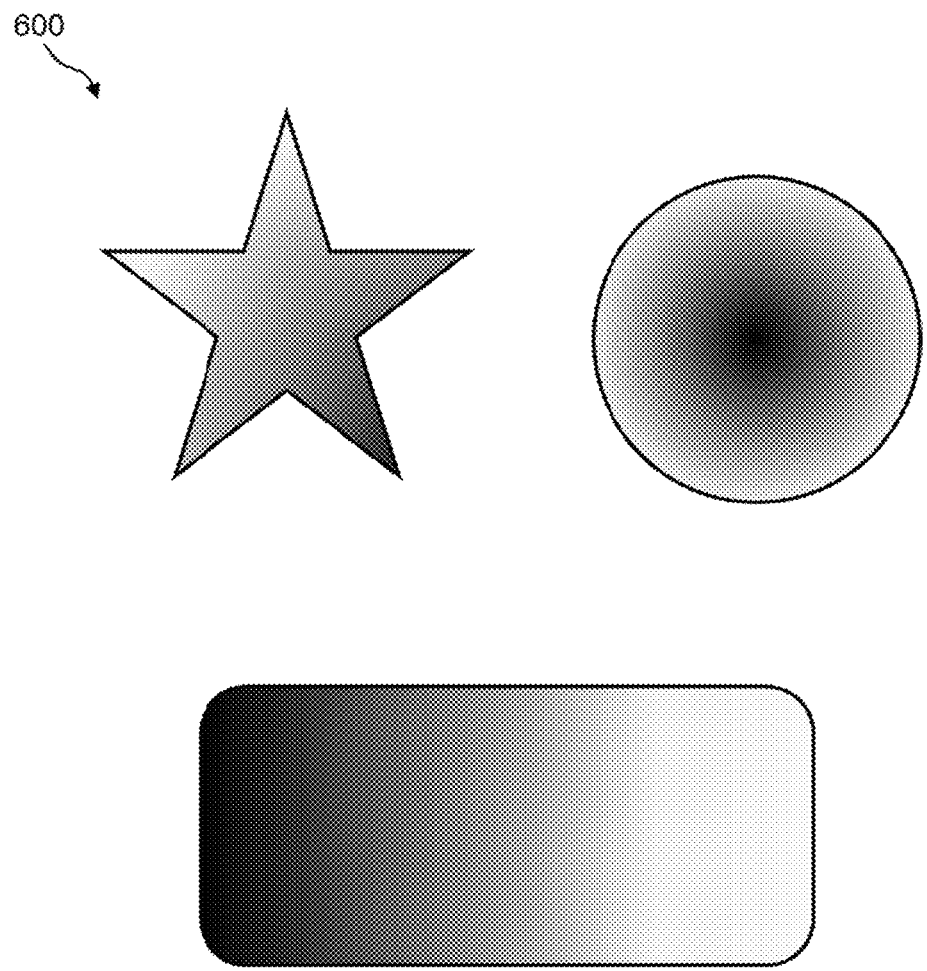
Figure 7:
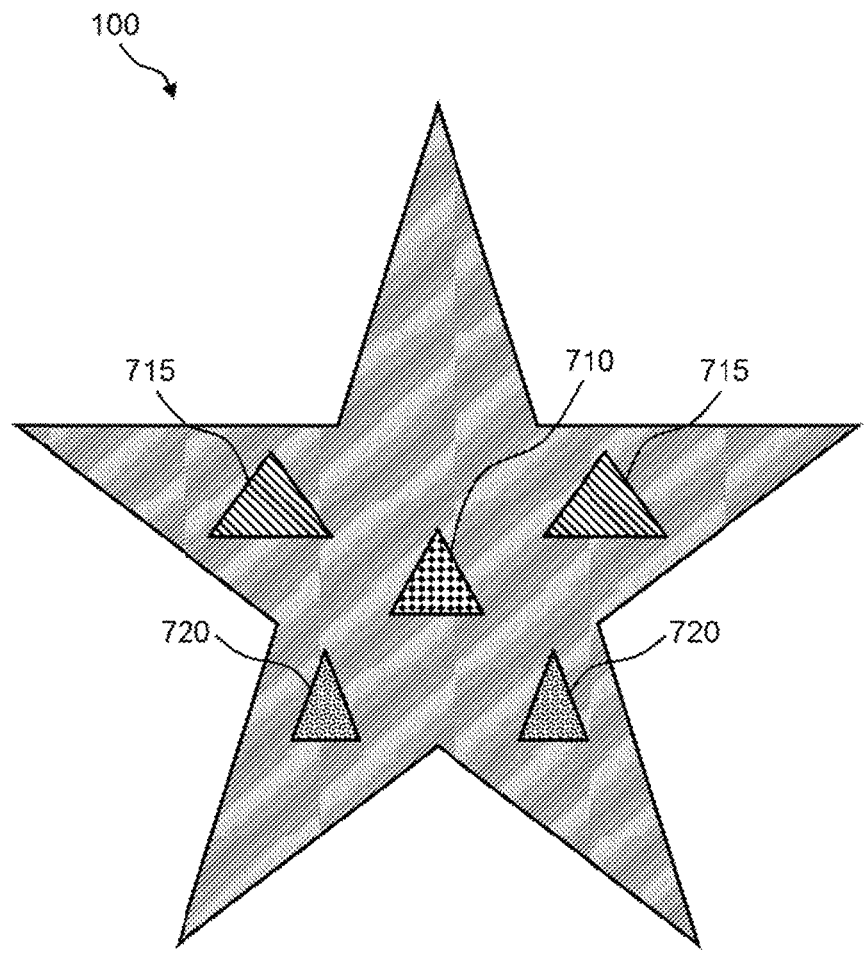
Figure 8A:
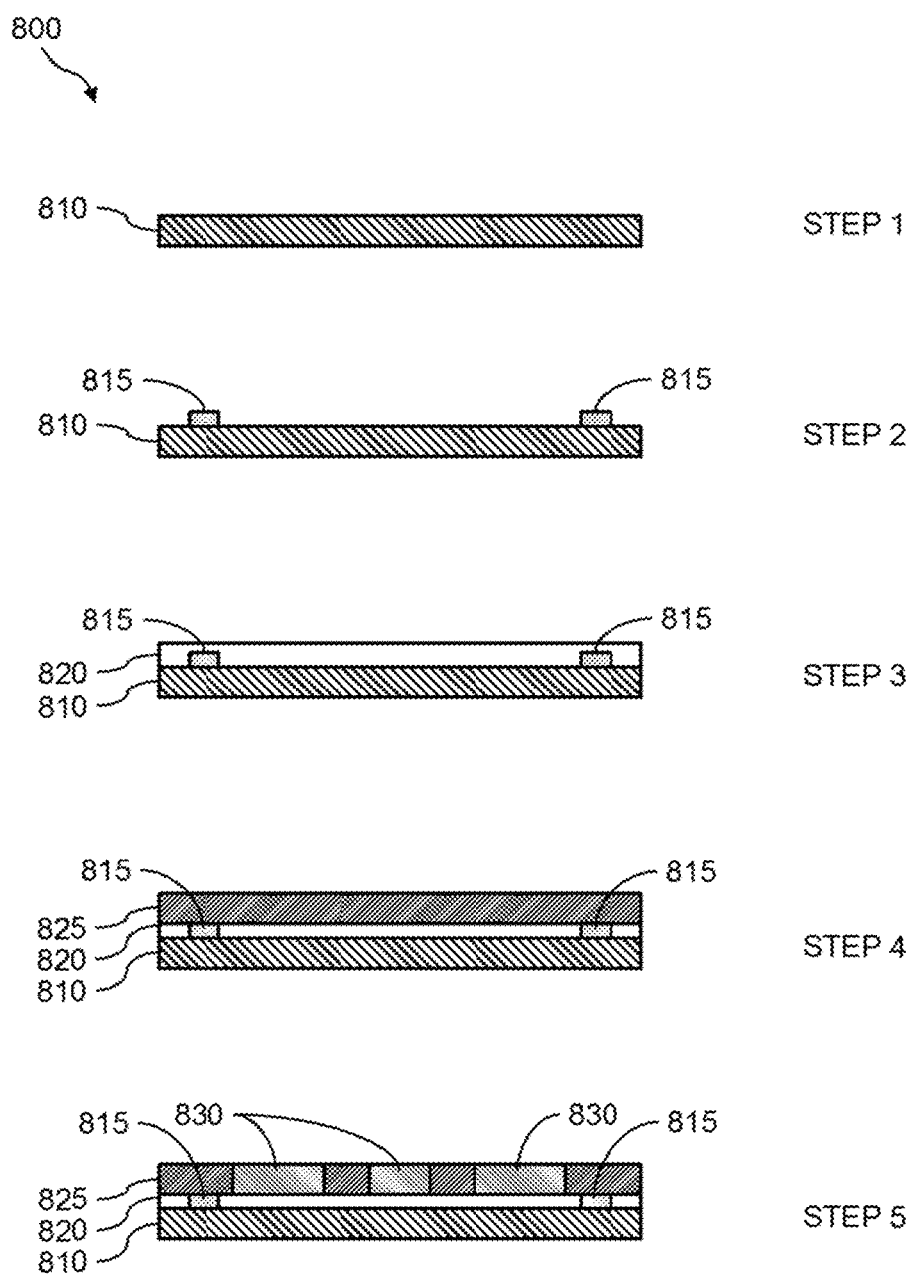
Figure 8B:
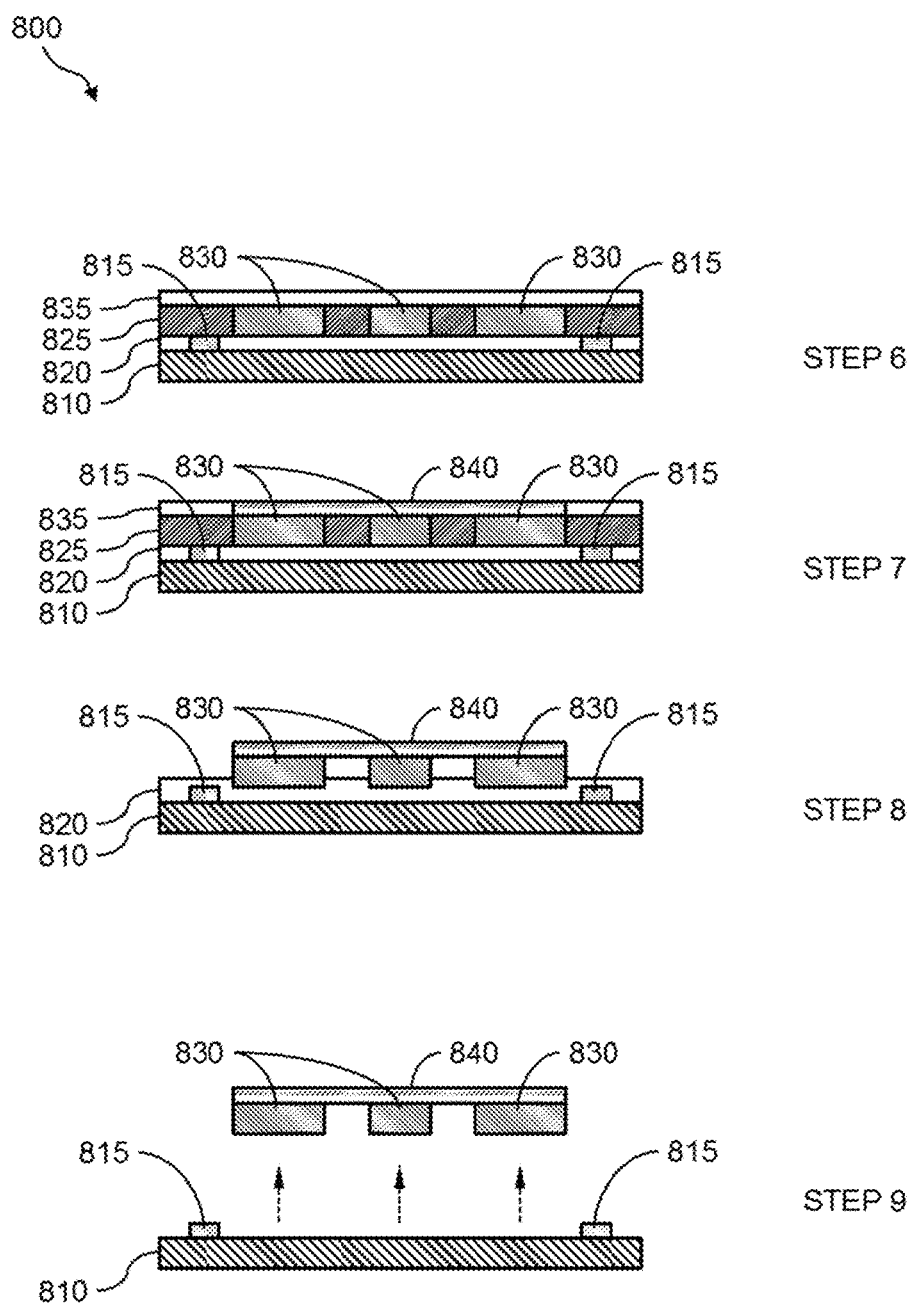
Figure 9:
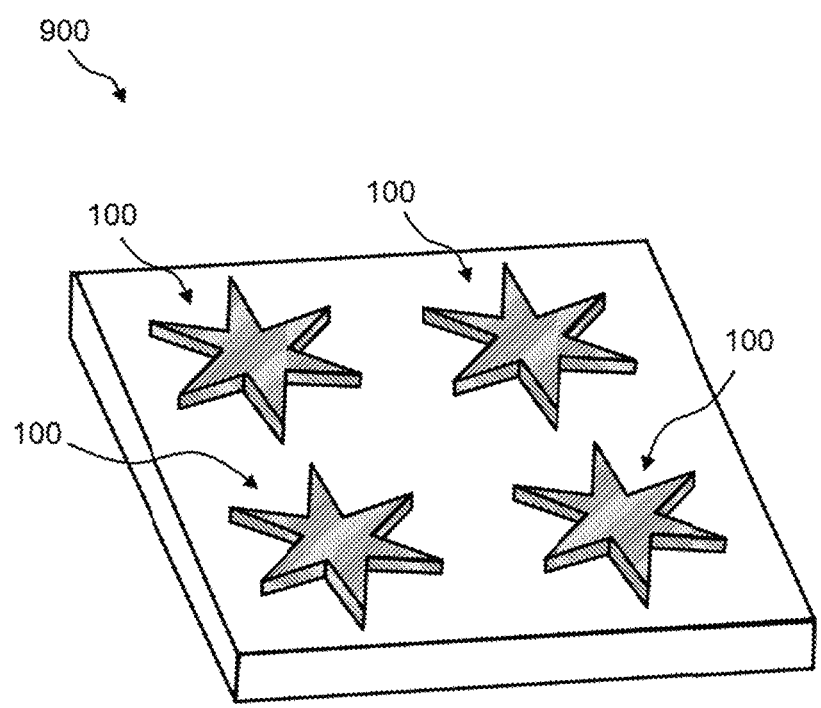
Figure 10A:
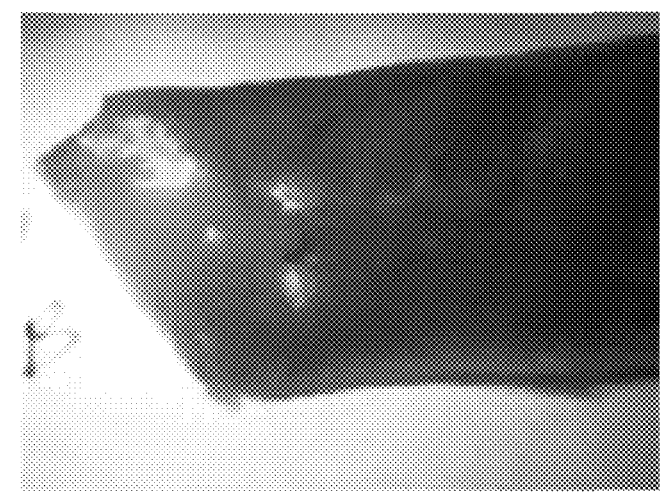
Figure 10B:
Figure 11:
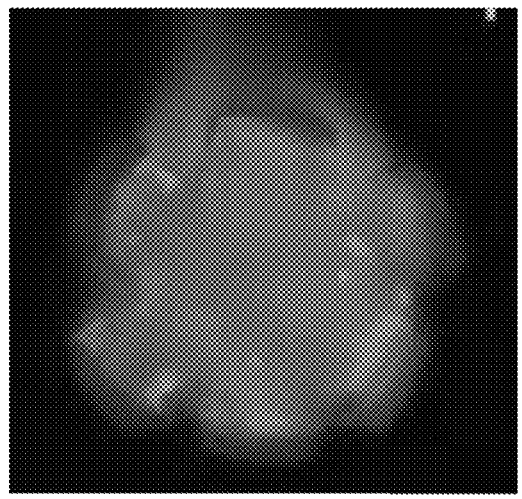
Figure 12:
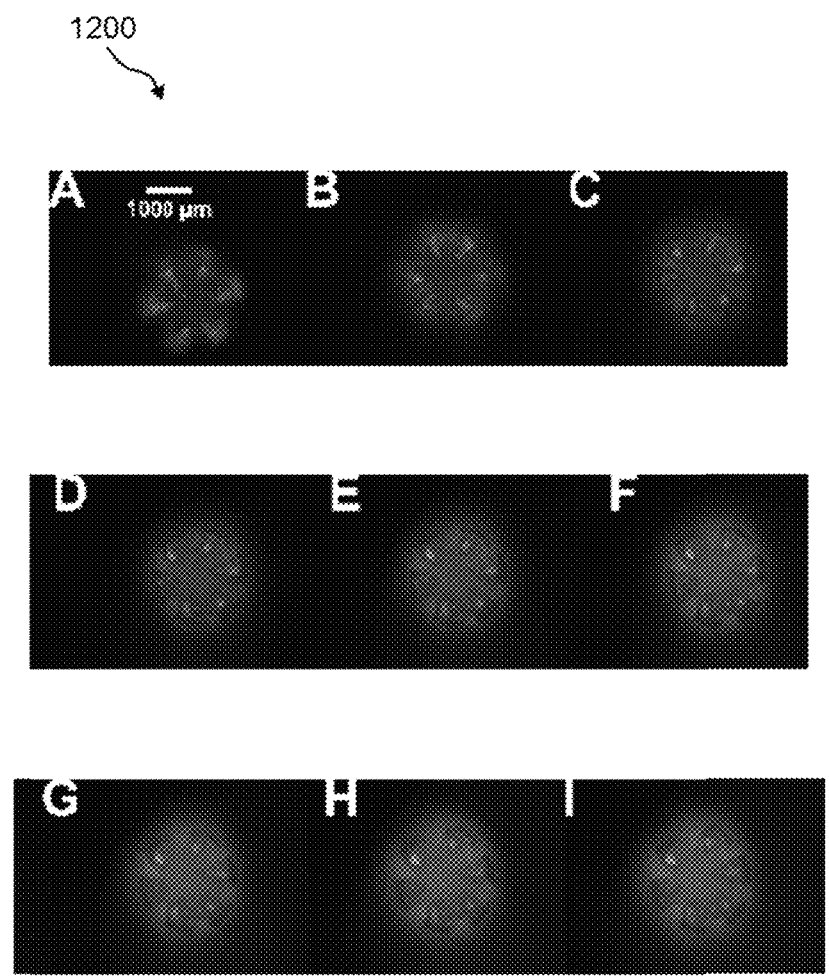

Having thus described the presently disclosed subject matter in general terms, reference will now be made to the accompanying Figures, which are not necessarily drawn to scale, and wherein:

FIG. 1A and FIG. 1B show views of the presently disclosed delivery system, referred to herein as a "theragripper" in an open state and in a closed state, respectively;

FIG. 2A, FIG. 2B, and FIG. 2C show other views of the presently disclosed theragripper in a fully open state, in a partially closed state, and in a closed state, respectively, and collectively depict a process of closing;

FIG. 3 shows views comprising steps A-L of an example of an actuation sequence of the presently disclosed theragrippers upon heating or cooling (fingers open and close in opposite directions);

FIG. 4A, FIG. 4B, and FIG. 4C show plan views of: (A) multi-fingered theragrippers that can include, for example, (B) flexible and/or rigid portions and/or (C) surface modifications;

FIG. 5A and FIG. 5B show plan views of multi-fingered theragrippers that depict fractal shaped and tip-modified designs;

FIG. 6 shows examples of the presently disclosed theragrippers fabricated with a drug or strain gradient;

FIG. 7 shows a plan view of an example of a multi-fingered theragripper that has multiple drugs patterned thereon to be released from the same theragripper;

FIG. 8A and FIG. 8B show an example of a representative process for fabricating the presently disclosed theragrippers using lithographical deposition and evaporation techniques;

FIG. 9 shows a perspective view of an example of a theragripper structure formed using the fabrication process shown in FIG. 8A and FIG. 8B;

FIG. 10A and FIG. 10B show images of in vitro dye evaluation on chicken breast with an ultraviolet lamp: (A) fluorescence of rhodamine 6G; and (B) fluorescence of fluorescein;

FIG. 11 shows an image of fluorescein release from the presently disclosed theragrippers; and FIG. 12 shows a time lapse photography sequence, including frames A, B, C, D, E, F, G, H, and I, demonstrating the in vitro drug eluting capacity of the presently disclosed theragrippers.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Hybrid Mechanical-Chemical Systems for Delivering Therapeutic Agents to Targeted Tissue The presently disclosed subject matter provides a relatively non-invasive and non-toxic, hybrid mechanical-chemical delivery system that allows for the sustained release of therapeutic agents within or in the proximity of a targeted or desired location or area of a subject's body. The presently disclosed hybrid mechanical-chemical delivery system comprises a mechanical component capable of being actuated to grasp tissue in a targeted or desired area of a subject's body and a chemical component capable of delivering one or more therapeutic agents, such as a drug, to the targeted or desired area. The presently disclosed hybrid mechanical-chemical delivery system is alternatively referred to herein as a "microtool," a "microgripper," a "therapeutic gripper," and/or a "theragripper."

There are several advantageous features of the presently disclosed theragrippers which allow for delivering at least one therapeutic agent directly to an affected area of the body. For example, the devices can be fabricated and actuated en-masse in a cost-effective and reliable manner. Also, the devices close in response to a change in local environment, such as body temperature, typically within five minutes which enables actuation in a wireless or tetherless manner. Further, the devices are relatively bio-inert and/or biodegradable to provide reduced risk if intentionally or unintentionally left behind. Further still, the devices are small enough to be deployed with standard surgical catheters or in drug delivery devices known in the art, for example a time-release capsule. Finally, the devices, in some embodiments, may possess magnetic elements allowing magnetic retrieval and in situ tracking.

The presently disclosed theragrippers can be designed to target and ultimately attach to a desired area or location in a subject's body that is afflicted with a disease, condition, disorder, or a symptom thereof. Further, the presently disclosed theragrippers can be deployed in a subject's body in numbers sufficient to improve the statistical likelihood of delivery to a targeted or desired area, and/or delivery of adequate doses of a therapeutic agent to the targeted or desired area.

The presently disclosed theragrippers are wireless and can be self-actuated by a variety of stimuli, including physical stimuli, such as a change in temperature and/or pH, and/or one or more biological or physiological cues, such as acids, enzymes, soluble proteins or surface biomarkers. The presently disclosed subject matter also provides methods for use of the drug delivery systems and treatment of a subject for a disease, condition, disorder, or combination thereof.

Because the presently disclosed theragrippers are free-standing and untethered, they can be ingested by the subject, e.g., via a sustained-release capsule, deployed to a diseased site via an invasive scope, such as an endoscope or laparoscope, or otherwise administered to the subject, e.g., via a suppository, enema or injection. After being administered to the subject, the theragrippers can be activated in response to a physical or biological cue to anchor the microgripper element of the theragripper to targeted or desired tissue, for example, diseased tissue in need of a therapeutic agent. In general, such theragrippers preferably mimic biological appendages, such as claws, and, in some embodiments, have flexible joints between rigid regions. The theragrippers may be any shape that may facilitate grasping of targeted tissue.

More particularly, the presently disclosed hybrid mechanical-chemical delivery devices are lithographically structured devices having an actuation layer and a control layer operatively connected to the actuation layer. The actuation layer includes a stress layer and a neutral layer that comprises materials and is configured such that it stores torsional energy upon being constructed. The control layer is configured to maintain the actuation layer substantially in a first configuration in a local environmental condition and is responsive to a change in the local environmental condition such that it permits a release of stored torsional energy to cause a change in a structural configuration of the lithographically structured device to a second configuration, the control layer thereby providing a trigger mechanism.

The energy required for the gripping action is intrinsically provided to the theragrippers as a consequence of either differential swelling of the films or residual stress stored in the joints and can be released when the hinges are softened (especially if polymeric) or otherwise loosened by heating, delamination or disintegration. As a result, the theragrippers require no wires, tethers or batteries to effectuate gripping. The theragrippers may be configured to be responsive to a number of stimuli including, but not limited to, temperature, presence of a chemical, such as an acid, enzymatic degradation, pH, soluble proteins, a surface biomolecule, such as biomarker, and the like. They can be actuated spontaneously in response to the specific environmental stimuli or triggered using a heat source such as a heat pad, infrared, radio-frequency or other electromagnetic field.

Thus, in some embodiments, the presently disclosed hybrid mechanical-chemical delivery device includes multiple layers configured to allow for the structural configuration of the device to change from a first configuration to a second configuration in response to a stimulus, such as a change in a local environmental condition. Change from the first configuration to the second configuration allows for the device to grasp tissue via release of stored torsional energy in one or more layers of the device. Accordingly, the presently disclosed theragrippers can curve or fold to hold onto or grip onto tissue and deliver therapeutic agents, such as a drug, to the targeted tissue over a prolonged, sustained, or extended period of time.

Mechanical portions, i.e., microgripper elements, of the presently disclosed theragrippers suitable for use with the presently disclosed theragrippers and methods are disclosed in International PCT Patent Application Publication No. WO 2012154511, which is incorporated herein by reference in its entirety. Further, representative microgrippers suitable for use with the presently disclosed subject matter are disclosed in International PCT Patent Application Publication No. WO 2009/111737, which is incorporated herein by reference in its entirety. Additional microgrippers suitable for use with the present invention are disclosed in Bassik et al. (J Am Chem Soc. 132:16314-7 (2010)), Leong et al. (Proc Natl Acad Sci USA 106:703-8 (2009)) and Randhawa et al. (J Am Chem Soc 130:17238-9 (2008)), the entire contents of which also are incorporated herein by reference.

For example, Bassik et al. demonstrated gripper-like devices that are similar to tiny hands, which exhibit the ability to respond to biological or physical cues, such as the presence of enzymes or a change in temperature, and thereby modify their conformation. Modification of the conformation of the gripper-like devices is similar to the closing action of the finger's in one's hand with the resulting "gripping" action.

The previously disclosed microgrippers could be introduced into the GI tract via endoscopy in an open state actuated wirelessly within the subject's body into a closed state. Gultepe, et al., Adv. Mater. (2013). It was demonstrated that such microgrippers could be removed with a magnetic field and used to retrieve tissue that can be used in cytologic, as well as molecular, diagnostic tests. For example, the microgrippers were used for retrieving tissues from difficult to reach areas in the GI tract, such as the bile duct in a porcine model (Gultepe, et al., Adv. Mater. (2013)) and in statistical sampling of large mucosal organs, such as the colon. Gultepe et al., Gastroenterology (2013). The previously disclosed microgrippers, however, were metallic with a polymeric layer that responds to biological or physical cues. In contrast, the presently disclosed microgrippers include therapeutic agents embedded in the polymeric layer, as well as the mechanical wireless actuation portion, hence the terminology "theragrippers." Further, methods for forming three-dimensional hydrogel or soft polymeric microstructures that exhibit self-folding in response to stimuli, such a change in pH, are disclosed in Guan et al., U.S. Patent Application Publication No. 2004/0191321 A1, for "Self-folding Polymer Microparticles," published Sep. 30, 2004, now U.S. Pat. No. 7,364,675, issued Apr. 29, 2008, and Guan et al. (2005), each of which is incorporated herein by reference in its entirety. Additionally, a self-folding drug delivery device made of a bilayered structure comprising a pH-sensitive hydrogel and a non-swelling layer, wherein the bilayer further comprises a mucoadhesive drug layer is described by He et al. (2006), which is incorporated herein by reference in its entirety.

Such devices known in the art, however, comprise soft materials, which likely would not sufficiently attach to, or grip, the mucosa of the GI tract to allow for the extended release of one or more therapeutic agents in the GI tract. Such deficiencies may be overcome by utilizing stiff polymers and/or highly crosslinked hydrogels. For example, polymers suitable for use in providing the necessary rigidity to the presently disclosed devices can have a modulus of greater than about 1 mPa. Consequently, stiff mechanical portions may be employed to provide theragrippers capable of adhering to more tissues for longer periods of time, as was previously unavailable in the art.

Accordingly, the presently disclosed hybrid mechanical-chemical delivery system comprises at least a mechanical portion and a chemical portion. Referring now to FIG. 1A, a representative theragripper 100 in an open configuration is provided. Theragripper 100, in some embodiments, includes a body 110, a plurality of fingers (or digits or appendages) 115, and a chemical portion 120 adapted to comprise and ultimately release one or more therapeutic agents to a targeted tissue site. In some embodiments, the plurality of fingers (or digits or appendages) has a range from about three fingers (or digits or appendages) to about 1,000 fingers (or digits or appendages) or more.

Chemical portion 120 can deliver a drug or other therapeutic agent to the tissue to which the theragripper is attached. Chemical portion 120 can, in some embodiments, comprise a porous polymer or gel-based thin film that adheres to the body 110 of the theragripper, or in some embodiments, the plurality of fingers (or digits or appendages) 115, or both the body 110 and fingers 115 (or digits or appendages). As used herein, the term "thin film" refers to a layer of material having a thickness ranging from fractions of a nanometer, e.g., a monolayer, to several micrometers in thickness.

Referring now to FIG. 1B, a representative theragripper 100 in a closed configuration is provided. In the closed configuration, the plurality of fingers (or digits or appendages) 115 can grasp and thereby attach to tissue 150. In such embodiments, chemical portion 120 can be in direct contact with tissue 150 or can release a therapeutic agent directly to or in the proximity or vicinity of tissue 150. In some embodiments, theragripper 100 can comprise one or more polymeric materials, and in some embodiments, can be completely comprised of one or more polymeric materials. Advantages of polymeric materials for use in the presently disclosed theragrippers are provided herein below.

FIGS. 2A-2C show other views of the presently disclosed theragripper in a fully open state (FIG. 2A), in a partially closed state (FIG. 2B), and in a closed state (FIG. 2C), respectively, thereby depicting a process of sequentially closing.

In some embodiments, the theragrippers have a star shape or a shape that comprises tips or fingers. In other embodiments, the theragrippers can be in the shape of a sphere or ball having sharp tips, spikes, or fingers. Any shape of the presently disclosed theragrippers that allow them to grab onto or otherwise grasp targeted or desired tissue in a subject is contemplated.

Referring now to FIGS. 4A-4C, a representative theragripper 100, e.g., a multi-finger theragripper 100 having a plurality of fingers (or digits or appendages) 115, in an open configuration is provided (FIG. 4A), which can include, in some embodiments, a plurality of rigid portions 130, in some embodiments, a plurality of flexible portions 135 (FIG. 4B), and, in some embodiments, a plurality of surface modifications 140 (FIG. 4C). In representative embodiments, the surface modifications can comprise patterns, protrusions, artificial cilia, or patches to enhance adhesion of theragripper 100 to tissue 150 and/or to increase the total surface area of theragripper 100 (FIG. 4C wherein the surface modifications are collectively illustrated as circles). Increasing the total surface area of theragripper 100 can in turn enhance adhesion of theragripper 100 to tissue 150 and/or increase its capacity (e.g., load) for the one or more therapeutic agents patterned thereon.

Referring once again to FIGS. 4B and 4C, one or more of the plurality of rigid portions 130, plurality of flexible portions 135, and/or plurality of surface modifications 140 can be present, either alone or in combination, in theragripper 100. One of ordinary skill in the art would recognize that the plurality of rigid portions 130 and plurality of flexible portions 135, if present, would both be present at the same time in representative embodiments.

Further, theragripper 100 can include hinges. In some embodiments, flexible portions 135 can include one or more hinges. In other embodiments, the characteristics of flexible portions 135 and rigid portions 130 can be reversed. That is, element(s) 135 can comprise a rigid portion and element(s) 130 can comprise a flexible portion. In such embodiments, element 130 can include one or more hinges.

Hinges suitable for use with the presently disclosed theragrippers are disclosed in International PCT Patent Application Publication No. WO 2012154511, which is incorporated herein by reference in its entirety. Hinges can be composed of, for example, gelatin, a polypeptide, or carboxymethylcellulose (CMC), a polysaccharide, and the like as disclosed in Bassik et al. 2010, which also is incorporated by reference in its entirety. Such hinges can include pre-stressed and structural metal films, and can be patterned using photolithography and combined with rigid segments to create a gripper. The hinges can curve when exposed to a stimulus trigger.

Referring now to FIGS. 5A and 5B, tip-modified theragrippers 500 comprising a plurality of fingers (or digits) 515 having star-shaped tips 525 (FIG. 5A) or circular-shaped tips 530 (FIG. 5B) are provided. It would be understood by those of ordinary skill in the art that in addition to the star-shaped tips 525 or circular-shaped tips 530 shown, the plurality of fingers 515 also could comprise tips and components of various other shapes and sizes, including for example other types of tapered tips and/or sharp tips generally that allow for optimal gripping of the theragripper to the desired tissue location.

Referring now to FIG. 6, various exemplary shapes of the presently disclosed theragrippers 100 fabricated with a therapeutic agent or biological strain, i.e., a genetic variant or subtype of a microorganism, gradient 600 are provided.

Referring now to FIG. 7, theragripper 100 can have a plurality of therapeutic agents patterned thereon, including, in some embodiments, first therapeutic agent 710, second therapeutic agent 715, and/or third therapeutic agent 720, each of which can be released simultaneously or sequentially from theragripper 100. Such embodiments can be used for combination therapeutics comprising more than one therapeutic agent or drug (for example, the different triangles 710, 715, and 720, in FIG. 7 are illustrated as different therapeutic agents). In further embodiments, the presently disclosed delivery system comprises a matrix, recess, and/or microwell that can comprise one or more therapeutic agents. In some embodiments, the therapeutic agent is a liquid and in other embodiments, the therapeutic agent is a solid.

The presently disclosed theragrippers can be fabricated via the lithographical deposition and evaporation of several layers. Referring now to FIG. 8A and FIG. 8B, a representative process for fabricating the presently disclosed theragrippers is provided. Both the chemical, matrix-like portion of the theragripper, which may elute one or more therapeutic agents over the course of, for example, days, as well as the wireless actuation layer, which responds to physical, biological, and/or physiological cues and results in the theragripper closing, are deposited in this fashion.

One of ordinary skill in the art would recognize that any known process can be used to fabricate the presently disclosed devices. For example, the presently disclosed devices can be fabricated by molding, three-dimensional printing, a layer-by-layer process, spin-coating photolithography, and the like. Accordingly, the lithographical deposition and evaporation process depicted in FIGS. 8A and 8B is a representative, non-limiting approach for preparing the devices. Importantly, such devices can be prepared with, for example, two polymer layers, each of which swell differently in an environment, i.e., so called "differential swelling," or can include a pre-stressed bilayer comprising a layer, e.g., a stimuli-responsive polymer, that can trigger a change in configuration or conformation.

Referring once again to FIG. 8A, in step 1 a silicon substrate 810 is provided. In step 2, Cr/Cu alignment markers 815 are evaporated onto silicon substrate 810. In step 3, a polyvinyl alcohol (PVA) sacrificial layer 820 is spincoated onto silicon substrate 810. In step 4, a poly(propylene fumarate) (PPF)/diethyl fumarate (DEF) layer 825 is spincoated onto sacrificial layer 820. In step 5, the PPF/DEF layer 825 is photolithographically patterned to form PPF/DEF pattern 830. In step 6, the PPF/DEF pattern 830 is coated with a stimuli-responsive polymer, e.g., NIPAM-AAc, layer 835, wherein NIPAM-AAc is a poly(N-isopropyl acrylamide) (PNIPAM) and acrylic acid (AAc) copolymer.

One of ordinary skill in the art would recognize that any stimuli-responsive polymer is suitable for use in the presently disclosed devices as a triggering mechanism for actuating the device to fold from one configuration or conformation to another. As referred to herein, a stimuli-responsive polymer, also referred to as "smart" polymers or "environmentally sensitive" polymers, can undergo a change in their microstructure, for example, from a hydrophilic to a hydrophobic state, triggered by changes in the environment. External stimuli, including, but not limited to, a change in temperature, a change in pH, ionic strength, magnetic and electric fields, light, ultrasound, and chemical species, can trigger changes in the environment. The macroscopic changes that occur in the micro structure generally are reversible. Therefore, the polymer is capable of returning to its initial state when the stimulus is removed. Classes of stimuli-responsive polymers can be characterized by their physical forms; (a) linear free chains in solution, (b) covalently cross-linked reversible and physical gels, and (c) chain adsorbed or surface-grafted forms.

Temperature and pH sensitivity are common properties utilized in stimuli-responsive polymers because: some disease states manifest themselves by a change in temperature and/or pH; and the response to the stimulus, e.g., temperature and/or pH, can be tuned to a desired temperature and/or pH range. The most extensively investigated temperature/pH sensitive systems are based on poly(N-isopropylacrylamide) (PNIPAM). PNIPAM can be chain-end functionalized with carboxylic acid, NHS ester, amine, and maleimide groups to develop a series of temperature- and pH-sensitive polymers. Further, NIPAM can be copolymerized with methacrylic acid to impart pH sensitivity. Also pH and temperature sensitive hydrogels can be prepared using NIPAM, acrylic acid and a di-acrylamide crosslinker. For example, PNIPAM exhibits a LCST of about 32° C. in aqueous solution, and the lower critical solubility temperature (LCST) can be easily manipulated by copolymerization of NIPAM with suitable monomers.

The presently disclosed devices also can be actuated by a heat source, such as a heat pad, infrared radiation, radio-frequency, or other electromagnetic field. Such embodiments involve the use of an external trigger/source to actuate the devices once they have reached the desired location. In yet other embodiments, the presently disclosed devices can include nano- or micro-scale additives within the device, such as magnetic nanoparticles to enable imaging, guidance, or remote triggering.

Referring once again to FIG. 8B, in step 7, the stimuli-responsive polymer, e.g., NIPAM-AAc, layer 835 is photo-lithographically patterned to form stimuli-responsive polymer, e.g., NIPAM-AAc, pattern 840. One or more therapeutic agents, e.g., one or more drugs, can be incorporated into the device, preferably in or on the patterned stimuli-response polymer layer 835 or pattern 840. More particularly, the one or more therapeutic agents can be incorporated into a thin film, porous material, capsule, or reservoir patterned onto stimuli-response polymer layer 835 or incorporated in the stimuli-response polymer layer 835 layer itself.

Referring once again to FIG. 8B, in step 8, the photo-lithographically patterned materials are developed in alcohol, and then in step 9, the sacrificial layer 820 is dissolved in water.

Referring now to FIG. 9, is an example of a structure 900 formed using the fabrication process presented in FIG. 8A and FIG. 8B. Structure 900 includes a plurality of theragrippers 100 formed by the presently disclosed process.

The presently disclosed theragrippers preferably are bio-inert, and also may be wholly or partially bioresorbable. For example, the theragrippers may be composed completely of bio-inert materials or may be coated with a bio-inert material. A number of bio-inert materials useful as coatings are well known in the art. In some embodiments, the theragrippers comprise an inert metal (such as gold), a polymer (such as polyimide, polyether ether ketone (PEEK), polytetrafluoroethylene, polyvinylidene fluoride, N-isopropylacrylamide (NIPAM), poly(propylene fumarate) (PPF) and polyamide), or a combination thereof. In still other embodiments, the mechanical gripping module comprises a polymer, a metal, or a combination thereof.

Certain polymeric materials also are biocompatible and biodegradable. Therefore, in some embodiments, the theragrippers are biodegradable. The term "biodegradable" as used herein is meant to refer to the characteristic of being able to be broken down by natural processes.

In further embodiments, the theragrippers are all-polymeric. The term "all-polymeric" is used herein to refer to a theragripper comprising a polymeric mechanical gripping module and a thin film on the mechanically gripping module that also is polymeric. The theragrippers also may comprise a chemical, a therapeutic agent, or a drug that will be delivered to a subject, which might not be polymeric, but also can be included in a polymeric matrix for sustained release.

At least one advantage of using all-polymeric theragrippers is that the polymeric material can be temperature responsive. Thus, the theragrippers may be designed to close in a specific direction on heating above a certain temperature, e.g., above 32° C. In such embodiments, the theragrippers can be stored in a cold or hot solution and allowed to fold completely. They can then be deployed to a desired location. As the temperature of the theragripper approaches the temperature of the desired location (for example, 37° C.), the theragrippers can unfold and then refold, thereby allowing them to adhere to targeted tissue by the gripping mechanism.

FIG. 3 shows an embodiment of the actuation of theragrippers in response to a change in temperature. Referring now to FIG. 3, an actuation sequence 300 is shown comprising steps A-L, which show views of the plurality of fingers (or digits), e.g., fingers (or digits) 115 from FIGS. 1 and 2, opening and closing in opposite direction upon heating or cooling, i.e., exposure to a thermal stimulus.

As can be seen in steps A-L of FIG. 3, upon heating above 32° C., the fingers close and when cooled below 32° C., the fingers open. Therefore, these theragrippers may be in a first configuration, e.g., an open configuration, outside the body, for example by storing and preparing the theragrippers in an environment below 32° C., and then actuate to a closed configuration when introduced into the body, which has a temperature of about 37° C. Previous work has shown that surgical grippers that were made to excise tissue from a subject can be taken on an ice bath and close on introduction into the body. Gultepe et al., Gastroenterology (2013). Typically, actuation occurs in response to temperature within about 5 minutes. A star-shaped theragripper is depicted in FIG. 3, although a variety of shapes are suitable for use with the presently disclosed subject matter, as discussed in more detail herein.

Further, the theragrippers may be configured to be responsive to a number of stimuli. In some embodiments, the stimulus is at least one physical, biological, or physiological cue selected from the group consisting of temperature, pH, a chemical, such as an acid, a biochemical, such as an enzyme, a soluble protein, and a surface biomarker. As used herein, "biomarker" refers to a characteristic that is an indicator of normal biologic processes, pathogenic processes, or pharmacologic responses to a therapeutic intervention. For example, a biomarker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule. As used herein, a "biochemical" is characterized by being produced by or involving a chemical reaction in a living organism.

As described hereinabove, the energy required for actuating the gripping action is intrinsically provided to the theragrippers as a consequence of residual stress stored in one or more joints and can be released when the hinges are softened (especially if polymeric) or otherwise loosened by heating, or are delaminated or disintegrated. As a result, the theragrippers require no wires, tethers or batteries to effectuate gripping.

Different sizes and/or shapes of theragrippers can be provided depending on the specific application and site within a subject where they will be deployed. In various embodiments, the theragrippers have a major dimension less than about 10, 9, 8, 7, 6, 5, 4, 3, 2 or 1 mm. In an exemplary embodiment, the major dimension is less than about 1, 0.9, 0.8, 0.7, 0.6, 0.5, 0.4, 0.2 or 0.1 mm. Due to their small millimeter or sub-millimeter size, a large number, e.g., hundreds, thousands, or more of the theragrippers can be dispersed in a small amount of liquid and moved by fluid flow.

Further, any number of theragrippers may be deployed within a body cavity. In various embodiments, 1 to 10, 1 to 50, 1 to 100, 1 to 250, 1 to 500, 1 to 1000 or more theragrippers are deployed and may be optionally retrieved from a body cavity. As such, one of skill in the art would understand that varying amounts of one or more therapeutic agents may be delivered as desired.

The presently disclosed theragrippers can remain at a desired location within the body. For example, a plurality of theragrippers may be deployed so as to remain within, for example, the GI tract or within any other diseased site for a prolonged period of time and therefore have delayed drug release capabilities.

As provided hereinabove, the presently disclosed theragrippers may be made having a dimension ranging from about 10 microns to about 1 mm. In some embodiments, the theragrippers are small enough to be introduced into a subject in a capsule or pill that can be taken orally. The term "capsule", as used herein, refers to a relatively stable shell, either hard-shelled or soft-shelled, that can be used to enclose a therapeutic agent or drug. The capsule or pill also can be coated to provide for a time release or sustained release of the theragrippers to a targeted or desired location or area within a subject's body. One of ordinary skill in the art would appreciate that the presently disclosed theragrippers can be combined with other packaging methods or delivery media for administration to a subject. In other embodiments, the theragrippers are small enough to be introduced using catheters into a subject, such as in the GI tract. In some embodiments, the number of theragrippers administered to a subject has a range of anywhere between about two to multiple million, or more, drug delivery systems.

The methodology and device of the presently disclosed subject matter may be used to deliver a therapeutic agent to any area of the body. Generally, theragrippers are deployed to a body cavity, such as a hollow organ of the body, for example, the gastrointestinal tract. As such, the term "cavity of a subject" is intended to refer to internal surfaces and spaces of the body, as well as external surfaces of the body. The presently disclosed methods enable the drug delivery systems to remain within the GI tract or at a diseased site for a sustained period of time allowing for improved delayed release capabilities.

In some embodiments, the tissue site is selected from the group consisting of the esophagus, stomach, duodenum, small intestine, and large intestine. However, the tissue site may be any tissue area that is capable of receiving the theragrippers. This includes, for example, diseased tissue, such as tissues selected from the group consisting of a tumor, fistula, and abscess. In further embodiments, the drug delivery systems may grasp non-diseased tissue. The terms "diseased tissue" or "diseased site" as used herein refer to any condition, dysfunction or disorder of that tissue or site that damages or interferes with the normal function of a cell, tissue, or organ. A "tumor," as used herein, refers to all neoplastic cell growth and proliferation, whether malignant or benign, and all precancerous and cancerous cells and tissues. A "fistula", as used herein, refers to an abnormal connection or passageway between two epithelium-lined organs or vessels. An "abscess", as used herein, refers to a collection of pus that has accumulated within a tissue because of an inflammatory process. The terms "non-diseased tissue" or "non-diseased site" are used herein to refer to a tissue or site that has normal function of a cell, tissue, or organ.

When treatment on or near the GI tract is desired, the presently disclosed methods also can be used to determine which tissue site along the GI tract the theragrippers will grasp. The biological cues may be different for different parts of the GI tract. For example, the pH in the stomach is much more acidic than in the rest of the GI tract, and therefore, pH as a biological cue may be used to actuate the theragrippers. As another example, a tumor in the GI tract may produce certain biomarkers, such as interleukin, that can be used as a biological cue for actuation of the theragrippers. As still another example, inflammatory bowel disease also may produce unique biomarkers that can be used to actuate the theragrippers and only deliver a drug to the affected sites in the GI tract. Also, if the theragrippers are in a capsule, the capsule may degrade in certain parts of the GI tract depending on its composition, thereby releasing the plurality of theragrippers at or near those parts of the GI tract that degraded the capsule.

The presently disclosed system and methods can be used for a variety of clinical applications. In some embodiments, the presently disclosed methods can be used for the delivery of any pharmaceutical drug, therapeutic agent, or medication within the GI tract, such as by an oral or rectal route. Almost all medications require more than a single dose. The presently disclosed methods may advantageously reduce the number of times that a medication is given to a patient. In addition, virtually all medications benefit from sustained delivery over many days or longer.

The medication delivered by the presently disclosed system may be used to treat other parts of the body, not only the GI tract. As examples, a drug for reducing high blood pressure or reducing the risk of a heart attack can be given weekly instead of daily using the presently disclosed theragrippers delivered to the GI tract or other area of the body. In other embodiments, the presently disclosed theragrippers are used to deliver GI oriented medications within the GI tract for local action at a diseased site. In still other embodiments, the presently disclosed methods are used for the therapeutic delivery of theragrippers for hemostasis within the GI tract. In further embodiments, the presently disclosed methods are used for the delivery of chemotherapy locally, such as within the biliary tree.

Although a preferred embodiment of the presently disclosed methods is for the theragrippers to be administered by an oral or rectal route, other methods of administering the presently disclosed drug delivery systems are envisioned by the disclosure herein. More particularly, the theragrippers may be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. As just one of many possible examples, fistulae are hard to treat systemically. The presently disclosed theragrippers may be injected locally at the fistula site to treat the fistula.

As used herein, the terms "therapeutic agent" or "drug" refer to any pharmaceutical agent, composition, gene, protein cell, molecule, or substance that can be used to treat, control or prevent a disease, medical condition or disorder. The term "treat" or "treating" includes abrogating, substantially inhibiting, slowing or reversing the progression of a condition, substantially ameliorating clinical or symptoms of a condition, and substantially preventing the appearance of clinical or symptoms of a condition.

The amount of a therapeutic agent that results in a therapeutic or beneficial effect following its administration to a subject, including humans, is a "therapeutic amount" or "pharmaceutically effective amount." The therapeutic or beneficial effect can be curing, minimizing, preventing, or ameliorating a disease or disorder, or may have any other therapeutic or pharmaceutical beneficial effect.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "disease" or "disorder," as used herein, refers to an impairment of health or a condition of abnormal functioning. The term "syndrome," as used herein, refers to a pattern of symptoms indicative of some disease or condition. The term "condition," as used herein, refers to a variety of health states and is meant to include disorders, diseases, or injuries caused by any underlying mechanism or disorder, and includes the promotion of healthy tissues and organs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth. The term "plurality" as used herein means "one or more."

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter. The following Example is offered by way of illustration and not by way of limitation.

Example 1

Chemical-Delayed Release of Drug-Like Compounds from Theragrippers

To render the chemical drug eluting films on the theragrippers, porous, salt/sugar/gas leaching techniques were applied to the film. The porous layer acts as a matrix, similar to what is currently used in the pharmaceutical industry for the delayed release of drugs. Colombo, et al. (2009). Different leaching processes can be used to engineer devices with a well-defined controlled release rate. A variety of dyes visible in white light, as well as in fluorescent light (such as methyl blue, acid black, brilliant green, rhodamine 6G and crystal violet) were used with the porous film of the theragrippers.

Initially, experiments were performed on chicken breast to evaluate the capacity of dyes to diffuse and to be visible under ultraviolet light. Referring now to FIGS. 10A and 10B are images 1000 and 1010 depicting an in vitro dye evaluation on chicken breast with an ultraviolet lamp, wherein image 1000 depicts fluorescence of rhodamine 6G and image 1010 depicts fluorescence of fluorescein. The fluorescence of rhodamine 6G (Panel A) and fluorescein (Panel B) were visible using an ultraviolet lamp. Fluorescein, because of its fluorescent properties, as well as its hydrophilic properties, can diffuse through tissues easily. It was found that fluorescein and rhodamine 6G performed superiorly compared to the other dyes tested. FIG. 11 shows an optical image 1100 of the in vitro release of fluorescein from the presently disclosed theragrippers.

Time lapse photography was used to demonstrate the in vitro drug eluting capacity of the presently disclosed theragrippers. Referring now to FIG. 12 is time lapse photography sequence 1200 at frames A, B, C, D, E, F, G, H, and I. The theragrippers were incubated in a 0.2% fluorescein solution overnight and then washed multiple times with water to get rid of excess fluorescein. The images were taken over 15 minutes. Frame A displays small bright spots in the PPF layer (the polymeric layer that effectuates the drug release) where the fluorescein was deposited. Frames B to I demonstrate drug elution of fluorescein, as the cloud of green fluorescence becomes larger.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Morishita, M. and N. A. Peppas, Is the oral route possible for peptide and protein drug delivery? Drug Discov Today, 2006. 11(19-20): p. 905-10.

Bassik, N., A. Brafman, A. M. Zarafshar, M. Jamal, D. Luvsanjav, F. M. Selaru, and D. H. Gracias, Enzymatically triggered actuation of miniaturized tools. J Am Chem Soc, 2010. 132(46): p. 16314-7.

Colombo, P., F. Sonvico, G. Colombo, and R. Bettini, Novel platforms for oral drug delivery. Pharm Res, 2009. 26(3): p. 601-11.

Siegel R, Rathuanbone M. Overview of controlled release mechanisms. In: Fundamentals and Applications of Controlled Release Drug Delivery (J. Siepmann, R. Siegel, M. Rathbone, eds). Controlled Release Society (2012).

Basit A W. Advances in colonic drug delivery. Drugs 65, 1991-2007 (2005).

Lissner D, Siegmund B. Ulcerative colitis: current and future treatment strategies. Digestive Diseases 31, 91-94 (2013).

Cheifetz A S. Management of active Crohn disease. Journal of the American Medical Association 309, 2150-2158 (2013).

Lee P I, Kim C-J. Probing the mechanisms of drug release from hydrogels. Journal of Controlled Release 16, 229-236 (1991).

Tao S L, Desai T A. Microfabricated drug delivery systems: from particles to pores. Advanced Drug Delivery Reviews 55, 315-328 (2003).

Lamprecht A, Yamamoto H, Takeuchi H, Kawashima Y. A pH-sensitive microsphere system for the colon delivery of tacrolimus containing nanoparticles. Journal of Controlled Release 104, 337-346 (2005).

Guan J J, Ferrell N, Lee L J, Hansford D J. Fabrication of polymeric microparticles for drug delivery by soft lithography. Biomaterials 27, 4034-4041 (2006).

de Leede L G J, de Boer A G, Portzgen E. Rate-controlled rectal drug delivery in man with a hydrogel preparation. Journal of Controlled Release 4, 17-24 (1986).

Guan J J, He H Y, Lee L J, Hansford D J. Fabrication of particulate reservoir-containing, capsulelike, and self-folding polymer microstructures for drug delivery. Small 3, 412-418 (2007).

Brazel C S, Peppas N A. Pulsatile local delivery of thrombolytic and antithrombotic agents using poly(N-isopropylacrylamide-co-methacrylic acid) hydrogels. Journal of Controlled Release 39, 57-64 (1996).

Tao S L, Desai T A. Gastrointestinal patch systems for oral drug delivery. Drug Discovery Today 10, 909-915 (2005).

He H Y, Guan J J, Lee J L. An oral delivery device based on self-folding hydrogels. Journal of Controlled Release 110, 339-346 (2006).

Dadsetan M, et al. A stimuli-responsive hydrogel for doxorubicin delivery. Biomaterials 31, 8051-8062 (2010).

Chirra H D, Desai T A. Multi-reservoir bioadhesive microdevices for independent rate-controlled delivery of multiple drugs. Small 8, 3839-3846 (2012).

Bernards D A, Lance K D, Ciaccio N A, Desai T A. Nanostructured thin film polymer devices for constant-rate protein delivery. Nanoletters 12, 5355-5361 (2012).

Gupta P, Vermani K, Garg S. Hydrogels: from controlled release to pH-responsive drug delivery. Drug Discovery Today 7, 569-579 (2002).

Chirra H D, Desai T A. Emerging microtechnologies for the development of oral drug delivery devices. Advanced Drug Delivery Reviews 64, 1569-1578 (2012).

Guan J, He H, Hansford D J, Lee L J. Self-folding of three-dimensional hydrogel microstructures. The Journal of Physical Chemistry B 109, 23134-23137 (2005).

Bassik N, Abebe B, Laflin K, Gracias D H. Photolithographically patterned smart hydrogel based bilayer actuators. Polymer 51, 6093-6098 (2010).

Ionov L. Soft microorigami: self-folding polymer films. Soft Matter 7, 6786-6791 (2011).

Shim T S, Kim S-H, Heo C-J, Jeon H C, Yang S-M. Controlled origami folding of hydrogel bilayers with sustained reversibility for robust microcarriers. Angewandte Chemie 51, 1420-1423 (2011).

Stoychev G, Zakharchenko S, Turcaud S, Dunlop J, Ionov L. Shape-programmed folding of stimuli-responsive polymer bilayers. ACS Nano 6, 3925-3934 (2012).

Gracias D H. Stimuli responsive self-folding using thin polymer films. Current Opinion in Chemical Engineering 2, 112-119 (2013).

Wu Z L, et al. Three-dimensional shape transformations of hydrogel sheets induced by small-scale modulation of internal stresses, Nature Communications, 4, 1586 (2013).

Leong T G, Randall C L, Benson B R, Bassik N, Stern G M, Gracias D H. Tetherless thermobiochemically actuated microgrippers. Proceedings of the National Academy of Sciences 106, 703-708 (2009).

Gultepe E R, Jatinder S., et al. Biopsy with thermally-responsive untethered microtools. Advanced Materials 25, 514-519 (2013).

Gultepe E, et al. Biologic tissue sampling with untethered microgrippers. Gastroenterology 144, 691-693 (2013).

Oh K S, Yuk S H. Hydrogels-based drug delivery system with molecular imaging. In: Biomedical Applications of Hydrogels Handbook (Ottenbrite R, Park K, Okano T, eds). Springer (2010).

Vilar G, Tulla-Puche J, Albericio F. Polymers and drug delivery systems. Current Drug Delivery 9, 367-394 (2012).

Langer R S, Peppas N A. Present and future applications of biomaterials in controlled drug delivery systems. Biomaterials 2, 201-214 (1981).

Gurny R, Doelker E, Peppas N A. Modelling of sustained release of water-soluble drugs from porous, hydrophobic polymers. Biomaterials 3, 27-32 (1982).

Shaikh R, Raghu R S T, James G M, Woolfson A D, Donnelly R F. Mucoadhesive drug delivery systems. J Pharm Bioallied Sci 3, 89-100 (2011).

Kremser C, Albrecht K, Greindl M, Wolf C, Debbage P, Bernkop-Schnurch A. In vivo determination of the time and location of mucoadhesive drug delivery systems disintegration in the gastrointestinal tract. Magnetic Resonance Imaging 26, 638-643 (2008).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A system for delivering one or more therapeutic agents to a tissue site in a subject, the system comprising:
   (a) an untethered mechanical gripping module having a dimension ranging from about 10 microns to about 1 mm and comprising a plurality of fingers comprising a plurality of sharp or tapered tips, wherein the fingers comprise a metal, a polymer having a modulus of greater than about 1 mPa, or combinations thereof, wherein the mechanical gripping module comprises at least an actuation layer and a control layer operatively connected to the actuation layer, wherein the actuation layer comprises a stress layer and a neutral layer and is configured to store torsional energy and wherein the control layer maintains the actuation layer substantially in a first configuration in a local environmental condition and intrinsically responds to a change in the local environmental condition from one or more stimuli thereby releasing the stored torsional energy of the actuation layer causing a change of the actuation layer to a second configuration, wherein the mechanical gripping module is adapted to close by curving or folding to grasp onto tissue at the tissue site when the actuation layer changes to the second configuration; and
   (b) a chemical module comprising a thin film, porous material, capsule, or reservoir patterned on the mechanical gripping module, wherein the thin film, porous material, capsule, or reservoir comprises the one or more therapeutic agents, wherein the chemical module is patterned onto or incorporated in the control layer.

2. The system of claim 1, wherein the thin film is polymer or gel based.

3. The system of claim 1, wherein the mechanical gripping module comprises a polymer, a metal, or a combination thereof.

4. The system of claim 1, wherein the system is all-polymeric.

5. The system of claim 4, wherein the system comprises N-isopropylacrylamide (NIPAM) and poly(propylene fumarate) (PPF).

6. The system of claim 1, wherein the system is biodegradable.

7. The system of claim 1, wherein the system has a shape selected from the group consisting of a star or a sphere having a plurality of fingers.

8. The system of claim 7, wherein the plurality of fingers has a range from about three to about 1000 fingers.

9. The system of claim 1, wherein the one or more stimuli is selected from the group consisting of a change in temperature, a change in pH, an acid, a biochemical, an enzyme, a soluble protein, and a surface biomarker.

10. The system of claim 9, wherein the change in temperature comprises changing the temperature above about 37° C.

11. The system of claim 10, wherein the change in temperature comprises changing the temperature above about 32° C.

12. The system of claim 1, wherein the system further comprises a matrix, recess, or microwell comprising the one or more therapeutic agents.

13. The system of claim 1, wherein the system comprises an origami folding system.

14. The system of claim 1, wherein the system comprises a self-folding and/or unfolding system.

15. The system of claim 1, wherein the untethered mechanical gripping module comprises a metal and the system further comprises one or more magnetic elements allowing magnetic retrieval of the untethered mechanical gripping module from the subject.

* * * * *